(12) United States Patent
Fukaya et al.

(10) Patent No.: US 6,740,218 B2
(45) Date of Patent: May 25, 2004

(54) GAS SENSOR

(75) Inventors: Kenji Fukaya, Chiryu (JP); Masanobu Yamauchi, Kariya (JP)

(73) Assignee: Denso Corporation, Aichi-Pref. (JP)

( * ) Notice: Subject to any disclaimer, the term of this patent is extended or adjusted under 35 U.S.C. 154(b) by 56 days.

(21) Appl. No.: 09/774,650

(22) Filed: Feb. 1, 2001

(65) Prior Publication Data
US 2001/0017057 A1 Aug. 30, 2001

(30) Foreign Application Priority Data

Feb. 1, 2000 (JP) ........................................ 2000-023847
Dec. 27, 2000 (JP) ........................................ 2000-397062

(51) Int. Cl.$^7$ ............................................. G01N 27/406
(52) U.S. Cl. ........................ 204/427; 204/408; 204/424
(58) Field of Search ................................ 204/421–429, 204/408

(56) References Cited

U.S. PATENT DOCUMENTS 5,895,591 A * 4/1999 Kojima et al.
6,261,429 B1 * 7/2001 Jach et al.
6,287,439 B1 * 9/2001 Kato et al.

FOREIGN PATENT DOCUMENTS

| EP | 0899562 A2 | 3/1999 |
| JP | 5-126789 | 5/1993 |
| JP | 11-44668 | 2/1999 |
| JP | 11-72471 | 3/1999 |

* cited by examiner

*Primary Examiner*—Kaj K. Olsen
(74) *Attorney, Agent, or Firm*—Nixon & Vanderhye, PC

(57) ABSTRACT

A gas sensing element comprises a solid electrolytic element, a measured gas sensing electrode provided on an outer surface of the solid electrolytic element, and a reference gas sensing electrode facing a reference gas chamber. A heater is accommodated in the reference gas chamber. A contact portion is provided on an outer cylindrical surface of the heater so that the contact portion is brought into contact with an inside surface of the solid electrolytic element defining the reference gas chamber. A heating peak position of the heater is in the vicinity of the contact portion.

2 Claims, 10 Drawing Sheets

COMPARATIVE EXAMPLE

CIRCUMFERENTIAL DIRECTION

CIRCUMFERENTIAL DIRECTION

GAS SENSOR

BACKGROUND OF THE INVENTION

This invention relates to a gas sensor employed in an exhaust gas system for an internal combustion engine of an automotive vehicle, for example, utilized for combustion control of the internal combustion engine.

The exhaust gas system for an internal combustion engine is usually equipped with a gas sensor. Combustion control of the internal combustion engine is performed based on a sensing signal of the gas sensor so as to enhance the efficiency of exhaust gas purification.

In general, the gas sensor has an activation temperature. The capability of generating an accurate sensing signal is only effected when the temperature of the gas sensor exceeds the activation temperature. Hence, a heater is generally incorporated in the gas sensor to obtain an accurate sensing value as early as possible in the startup stage of the internal combustion engine.

According to recent enhancement of exhaust gas regulations, gas sensors are strongly required to increase their warm-up abilities compared with those of conventional gas sensors.

For example, to realize prompt activation, it is effective to increase a heat generation amount of the heater so as to shorten a time required for the gas sensor to reach its activation temperature.

As a method for increasing the heat generation amount of the heater, it may be effective to select a material having a small electric resistive value for a heat generating section to be accommodated into the heater.

However, excessively increased heat generation will induce large thermal shock in the heater, represented by generation of cracks. Furthermore, it is known that excessive heat generation induces early deterioration of the heater. In view of the foregoing, merely increasing the heat generation amount of the heater is not desirable to realize the prompt activation.

SUMMARY OF THE INVENTION

In view of the foregoing problems of the prior art, the present invention has an object to provide a gas sensor capable of realizing prompt activation without causing adverse effects of heat generation, such as thermal shock.

To accomplish the above and other related objects, the present invention provides a first gas sensor comprising a gas sensing element including a cup-shaped cylindrical solid electrolytic element having a reference gas chamber defined therein, a measured gas sensing electrode provided on an outer surface of the solid electrolytic element, and a reference gas sensing electrode provided on an inner surface of the solid electrolytic element facing said reference gas chamber, and a heater accommodated in the reference gas chamber. According to the first gas sensor, a contact portion is provided on an outer cylindrical surface of the heater so that the contact portion is brought into contact with an inside surface of the reference gas chamber, and a heat generating peak position of the heater is in the vicinity of the contact portion.

The most remarkable feature of the first gas sensor of the present invention is that the heat generating peak position of the heater is in the vicinity of the contact portion where the outer cylindrical surface of the heater is brought into contact with the inside surface of the reference gas chamber.

The present invention characterized by the above-described features operates in the following manner.

According to the first gas sensor of the present invention, the heat generating peak position of the heater is in the vicinity of the contact portion.

The contact portion is a portion where the heater is brought into contact with the inside surface of the solid electrolytic element. In other words, the contact portion is a portion where thermal energy of the heater is most effectively transferred to the gas sensing element.

Accordingly, even if the heat generation amount of the heater is the same as that of a conventional heater, generated heat of the heater can be effectively used to warm up the gas sensing element. Thus, it becomes possible to realize prompt activation without adverse effects of heat generation or thermal shock including deterioration of the gas sensing element and the heater.

The heat generating peak position of the heater is a position where the temperature of the heater is highest as shown in FIG. 4.

Thus, according to the first gas sensor of the present invention, it becomes possible to realize prompt activation without causing adverse effects of heat generation, such as thermal shock.

According to the first gas sensor in accordance with the present invention, a heater as shown in FIG. 3 comprises a ceramic core rod and a ceramic sheet wound around this core rod. In general, a heat generating section and a lead section made of an electrically conductive paste are printed on the ceramic sheet.

The components of the electrically conductive paste constituting the heat-generating portion are W, W—Mo, W—Re, Pt etc.

The contact portion provided on the outer cylindrical surface of the heater, as shown in FIG. 1, may be an annular portion formed at the distal end of the heater which is coaxially disposed with respect to the gas sensing element in the reference gas chamber. Alternatively, it is preferable that, as shown in FIG. 10, the contact portion may be a local spot on the outer surface of the heater.

The first gas sensor of the present invention can be used for various purposes, such as combustion control of an internal combustion engine. Furthermore, the present invention is widely applicable to all of the sensors which are equipped with a heater placed in an inside space of a sensor element.

Next, the present invention provides a second gas sensor comprising a gas sensing element including a cup-shaped cylindrical solid electrolytic element having a reference gas chamber defined therein, a measured gas sensing electrode provided on an outer surface of the solid electrolytic element, and a reference gas sensing electrode provided on an inner surface of the solid electrolytic element facing said reference gas chamber, and a heater accommodated in the reference gas chamber. According to the second gas sensor, the heater has a heat generating section for generating heat in response to electric power supplied thereto, and an electric resistive value of the heat generating section is maximized in the vicinity of the contact portion (refer to later-described FIG. 9) where the heater is brought into the gas sensing element.

With this arrangement, the heat generation amount increases in the vicinity of the contact portion of the heater. The gas sensing element can be effectively heated. The activation time can be shortened.

Accordingly, even if the heat generation amount of the heater is the same as that of a conventional heater, the generated heat of the heater can be effectively used to warm up the gas sensing element. Thus, it becomes possible to realize the prompt activation without adverse effects of heat generation or thermal shock including deterioration of the gas sensing element and the heater.

Thus, according to the second gas sensor of the present invention, it becomes possible to provide a gas sensor capable of realizing prompt activation without causing adverse effects of heat generation, such as thermal shock.

To form the portion of a ceramic heater where the electric resistive value r is maximized, as shown in later-described FIG. 4A, there is a method for increasing the electric resistance by partly narrowing a line width of the heat generating section at a portion corresponding to the heat generating peak position of the heater.

Furthermore, there is another method of increasing the electric resistance by partly thinning a thickness of the heat generating section at a portion corresponding to the heat generating peak position of the heater.

Furthermore, there is another method of increasing the electric resistance by partly using a different material having a high electric resistance for the heat generating section at a portion corresponding to the heat generating peak position of the heater (refer to later-described FIG. 9).

Next, the present invention provides a third gas sensor comprising a gas sensing element including a cup-shaped cylindrical solid electrolytic element having a reference gas chamber defined therein, a measured gas sensing electrode provided on an outer surface of the solid electrolytic element, and a reference gas sensing electrode provided on an inner surface of the solid electrolytic element facing the reference gas chamber, and a heater accommodated in the reference gas chamber. According to the third gas sensor, a heat generating section of the heater has a heat line pattern whose density is maximized in the vicinity of a contact portion (refer to later-described FIG. 11) where the heater is brought into said gas sensing element.

With this arrangement, the heat generation density increases in the vicinity of the contact portion of the heater. The gas sensing element can be effectively heated. The activation time can be shortened.

Accordingly, even if the heat generation amount of the heater is the same as that of a conventional heater, the generated heat of the heater can be effectively used to warm up the gas sensing element. Thus, it becomes possible to realize the prompt activation without adverse effects of heat generation or thermal shock including deterioration of the gas sensing element and the heater.

Thus, according to the third gas sensor of the present invention, it becomes possible to realize prompt activation without causing adverse effects of heat generation, such as thermal shock.

To maximize the pattern density (i.e., density of a heater line pattern) of the heat generating section of the ceramic heater as described above, there is a method for forming a heat generation section in a concentrated manner to form the heat generating peak position, for example, as shown in later-described FIG. 11.

Next, the present invention provides a fourth gas sensor comprising a gas sensing element including a cup-shaped cylindrical solid electrolytic element having a reference gas chamber defined therein, a measured gas sensing electrode provided on an outer surface of the solid electrolytic element, and a reference gas sensing electrode provided on an inner surface of the solid electrolytic element facing the reference gas chamber, and a heater accommodated in the reference gas chamber. According to the fourth gas sensor, the heater has a heat generating section for generating heat in response to electric power supplied thereto, and the heat generating section has a high resistive portion provided closer to a proximal end of the gas sensor.

Providing the high resistive portion of the heat generating section closer to the proximal end of the gas sensor in this manner makes it possible to moderate the heat generating peak so as not to cause sudden increase as shown in FIG. 12. It becomes possible to suppress the temperature increase in the vicinity of the heat generating peak. An overall temperature distribution becomes uniform.

Thus, according to the fourth gas sensor of the present invention, it becomes possible to realize prompt activation without causing adverse effects of heat generation, such as thermal shock.

Next, the present invention provides a fifth gas sensor comprising a gas sensing element including a cup-shaped cylindrical solid electrolytic element having a reference gas chamber defined therein, a measured gas sensing electrode provided on an outer surface of the solid electrolytic element, and a reference gas sensing electrode provided on an inner surface of the solid electrolytic element facing the reference gas chamber, and a heater accommodated in the reference gas chamber. According to the fifth gas sensor, the heater has a heat generating section for generating heat in response to electric power supplied thereto. A contact portion is provided on an outer cylindrical surface of the heater so that the contact portion is brought into contact with an inside surface of the reference gas chamber. And, a heat generating peak position of the heater appears within ¾ of a line segment extending between a distal end of a heat generating pattern closer to the contact portion and a center of the heat generating pattern for more than one fifth of a time required for the heat generating peak position of the heater to reach 900° C.

Providing the heat generating portion satisfying the above conditions makes it possible to effectively use the generated heat of the heater to warm up the gas sensing element even if the heat generation amount of the heater is the same as that of a conventional heater. Thus, it becomes possible to realize the prompt activation without adverse effects of heat generation or thermal shock including deterioration of the gas sensing element and the heater.

If the heat generating peak position exists within the above ¾ line segment region for a short duration less than one fifth of the time required for the heat generating peak position to reach 900° C., the activation of the gas sensing element will be delayed.

Furthermore, it is desirable that the heat generating peak position remains within the above ¾ line segment region until the heat generating peak position reaches 900° C.

Furthermore, if the heat generating peak position is offset toward the center of the heat generating pattern out of the above ¾ line segment region for more than one fifth of the time required for reaching 900° C., the activation of the gas sensing element will be delayed.

Thus, according to the fifth gas sensor of the present invention, it becomes possible to realize prompt activation without causing adverse effects of heat generation, such as thermal shock.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF PREFERRED EMBODIMENTS

First Embodiment

A gas sensor in accordance with a preferred embodiment of the present invention will be explained with reference to FIGS. 1 to 9.

Figure 1:
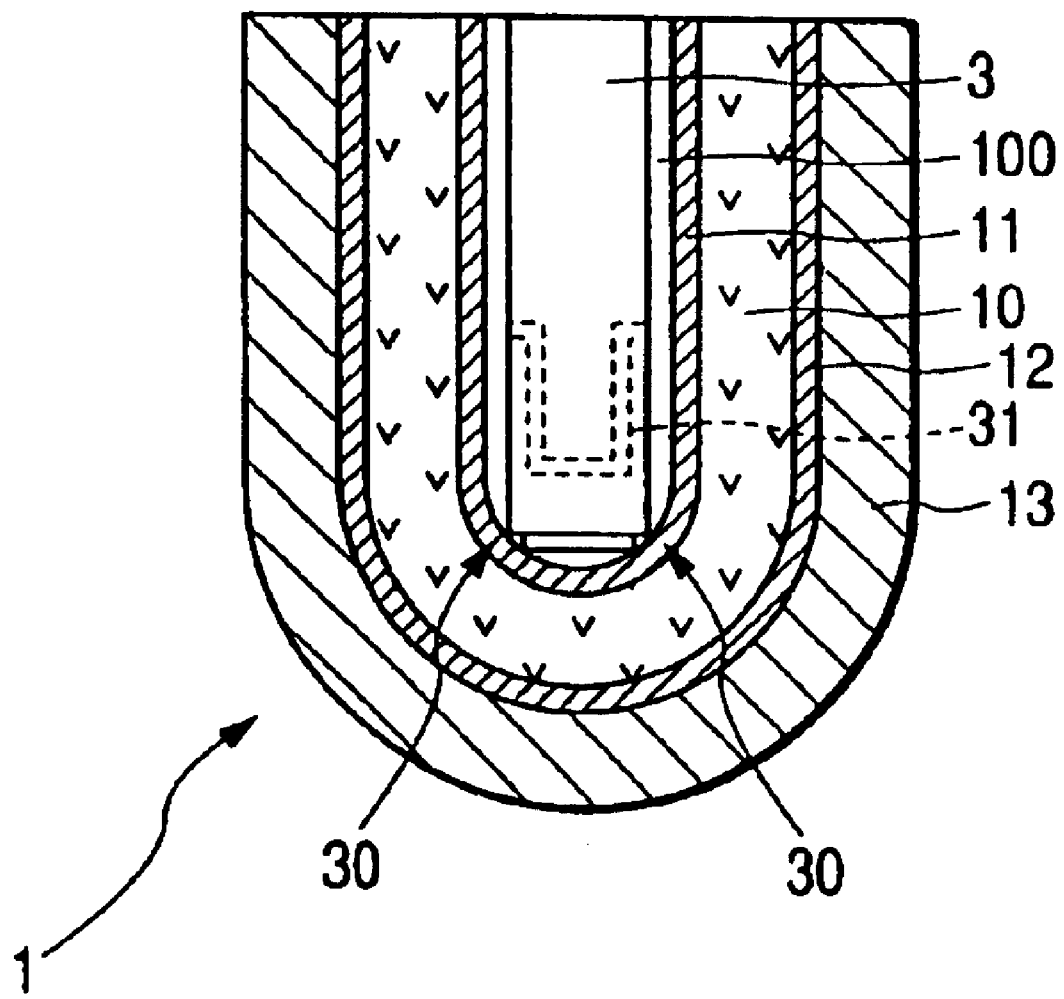
FIG. 1 is a cross-sectional view showing an essential structure of a gas sensing element in accordance with a first embodiment of the present invention.
Figure 2:
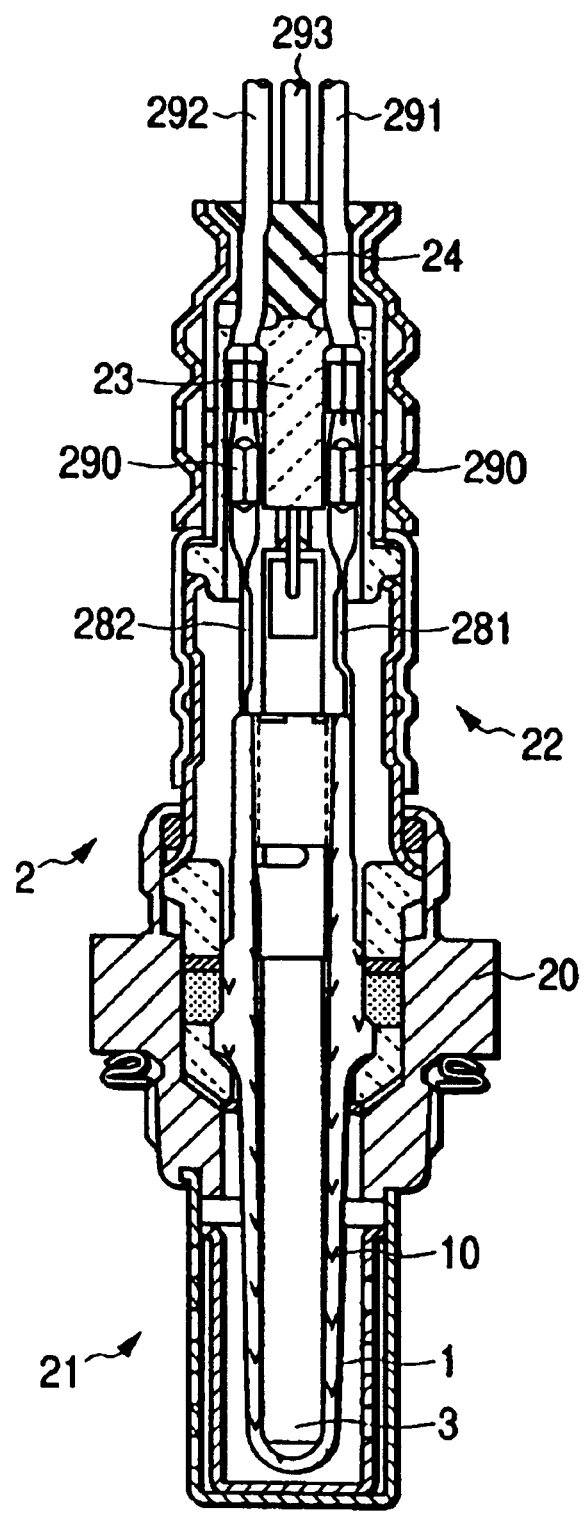
FIG. 2 is a vertical cross-sectional view showing an arrangement of a gas sensor in accordance with the first embodiment of the present invention.

As shown in FIGS. 1 and 2, a gas sensor 2 of this embodiment comprises a gas sensing element 1. The gas sensing element 1 includes a cup-shaped cylindrical solid electrolytic element 10 having a reference gas chamber 100 defined therein. A measured gas sensing electrode 12 is provided on an outer surface of the solid electrolytic element 10. A reference gas sensing electrode 11 is provided on an inner surface of the solid electrolytic element 10. The reference gas sensing electrode 11 faces the reference gas chamber 100. A heater 3 is accommodated in the reference gas chamber 100.

A contact portion 30 is provided on an outer cylindrical surface of the heater 3. The contact portion 30 is brought into contact with the inside surface of the reference gas chamber 100. A heat generating peak position (refer to FIG. 4A) of the heater 3 is in the vicinity of the contact portion 30.

The contact portion 30, as apparent from FIG. 1, is an annular perphery of the heater 3 along which a distal end of the heater 3 is brought into contact with the inside surface of the reference gas chamber 100 at a portion closer to the bottom of the reference gas chamber 100. As shown in FIG. 1, a porous protective layer 13 covers an outside surface of the measured gas sensing electrode 12 of the gas sensing element 1.

Hereinafter, the gas sensor 2 of the first embodiment will be explained in detail. According to the gas sensor 2 of this embodiment, the gas sensing element 1 is inserted and placed in a housing 20 as shown in FIG. 2. A measured gas side cover 21, having a double-layer structure, is disposed at a distal end side of the housing 20 to cover the distal end side of the gas sensing element 1. An atmosphere side cover 22 is disposed at a proximal end side of the housing 20 to cover the proximal end side of the gas sensing element 1.

An insulator 23 and a rubber bush 24 are located in an inside space of the atmosphere side cover 22. Each of the insulator 23 and the rubber bush 24 has a plurality of through holes provided therein. Sensor output terminals 281 and 282 of the gas sensing element 1 and lead wires 291 and 292 are disposed in these through holes. The lead wires 291 and 292 are connected to the sensor output terminals 281 and 282 by means of joint metal fittings 290. A lead wire 293 is provided to supply electric power to the heater 3.

Figure 3:
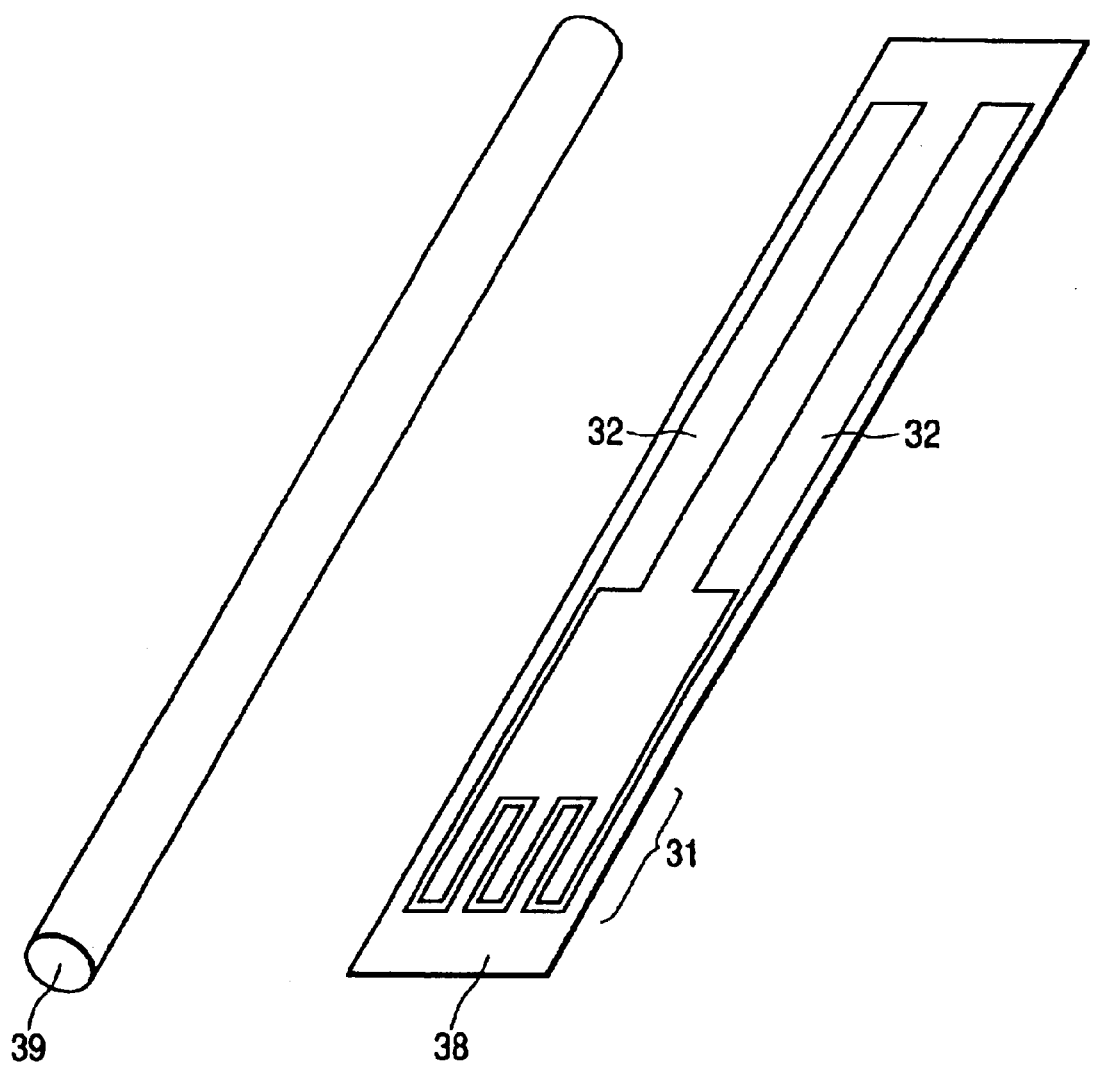
FIG. 3 is a development view showing a heater incorporated in the gas sensor in accordance with the first embodiment of the present invention.

The heater 3, as shown in FIG. 3, comprises a ceramic core rod 39 and a ceramic sheet 38. The ceramic sheet 38 is wound around the ceramic core rod 39. A heat generating section 31 and a lead section 32, both are made of an electrically conductive paste, are printed on the ceramic sheet 38. The electrically conductive paste contains tungsten and rhenium. The heat generating section 31 configures a heat generating pattern consisting of a heater line alternately folded at relatively small pitches.

The heater 3 is disposed coaxially with respect to the gas sensing element 1 as shown in FIG. 1. The configuration of the heat generating section 31 will be explained in more detail with reference to FIG. 4A. The heat generating section 31 has a narrowed width at the distal end of the heater 3.

Figure 4A:
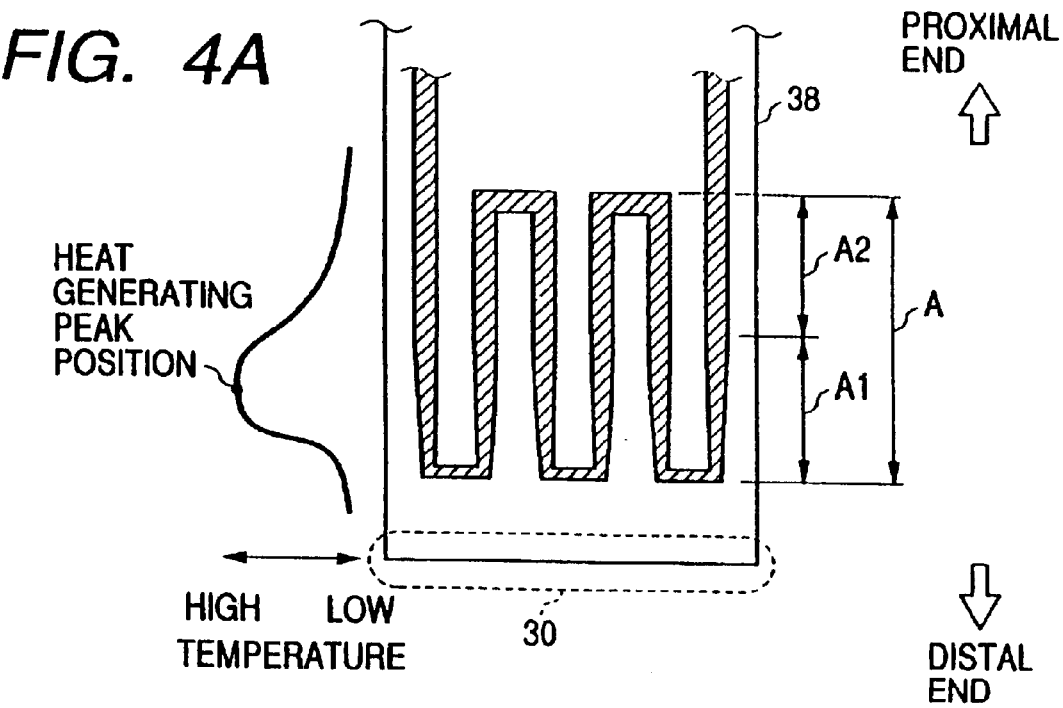
FIG. 4A is a view showing a detailed configuration of a heat generating section of the heater incorporated in the gas sensor in accordance with the first embodiment of the present invention.

The heat generating section 31 is indicated by a region "A" in FIG. 4A. The region "A" includes a distal region A1 and a proximal region A2. Both of the distal region A1 and the proximal region A2 are made of a W-Re alloy. The distal region A1 is thin in width compared with the proximal region A2. A resistance value of the distal region A1 is 1.2 Ω. A resistance value of the proximal region A2 is 1.0 Ω. Both of the distal region A1 and the proximal region A2 have the same axial length of 3 mm. In FIG. 4A, the contact portion 30 of the heater 3 is encircled by a dotted line.

FIG. 4A shows a temperature distribution at the heat generating section 31 observed when electric power is supplied to the heater 3.

As apparent from the temperature distribution shown in this drawing, the heat generating peak position appears at a distal end side of the heat generating section 31 offset forward with respect to the center of the heat generating section 31. The heat generating peak position is a position where the temperature is maximized.

The following is the comparison of performance between the gas sensor in accordance with this embodiment and a comparative gas sensor.

The evaluated gas sensor of this embodiment has the structural features disclosed in FIGS. 1 to 3 and 4A. The comparative gas sensor differs from this embodiment in the configuration of the heat generating section.

Figure 4B:
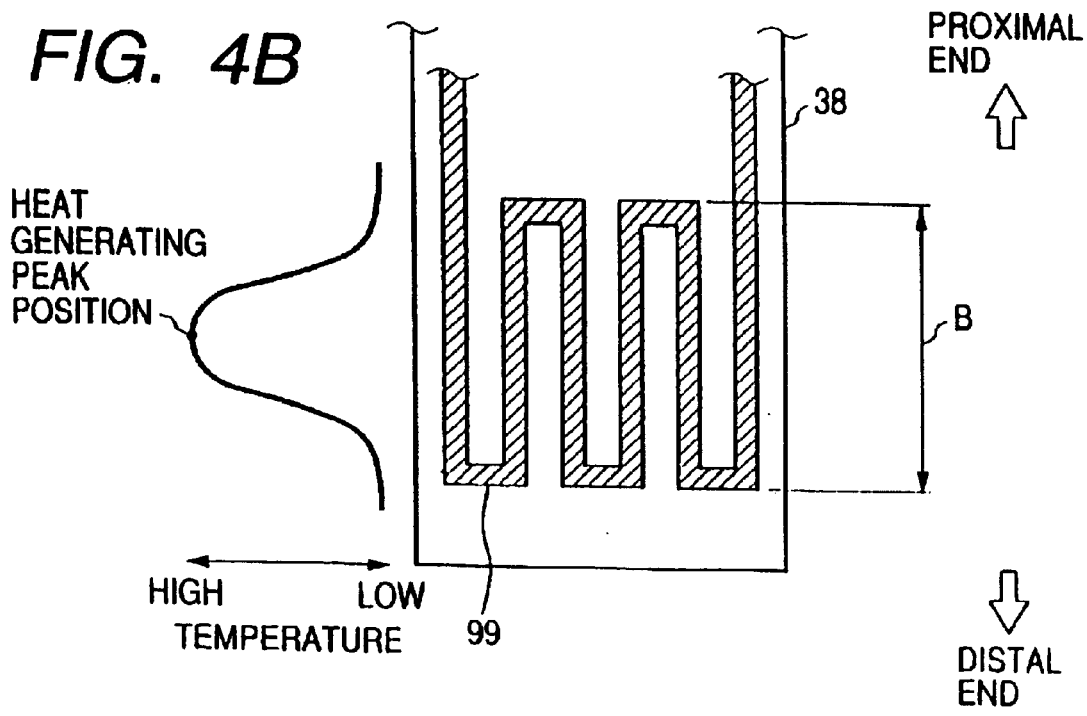
FIG. 4B is a view showing a detailed configuration of another heat generating section of the heater incorporated in the gas sensor in accordance with the first embodiment of the present invention.

FIG. 4B shows a region B indicating a heat generating section 99 of the comparative gas sensor. The width of the heat generating section 99 is uniform in the entire region from the distal end side to the proximal end side.

According to an evaluation test, the heat generating peak position of the heat generating section 99 appears at approximately the center of the heat generating section 99.

Figure 5:
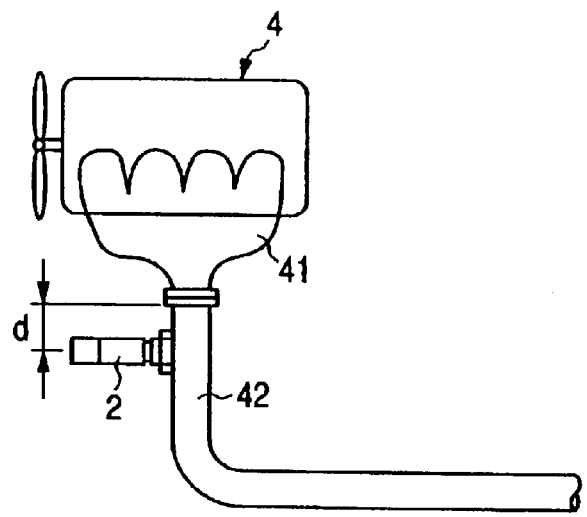
FIG. 5 is a view showing the gas sensor installed in an exhaust gas passage of an internal combustion engine in accordance with the first embodiment of the present invention.

As shown in FIG. 5, each of two gas sensors is located downstream at a distance d=5 cm from a joint portion between a manifold 41 of an internal combustion engine 4 and an exhaust gas pipe 42. A total volume of combustion chambers of this engine is 2.2 liters.

An operation of the internal combustion engine 4 is started from a cold state. After the engine 4 has started its operation, the temperature of the exhaust gas gradually increases. The gas sensor 1 is exposed to the exhaust gas, while the gas sensor 1 is heated from the inside thereof by the heater 3. Thus, the temperature of the gas sensor gradually increases. The sensor output is produced.

Figure 6:
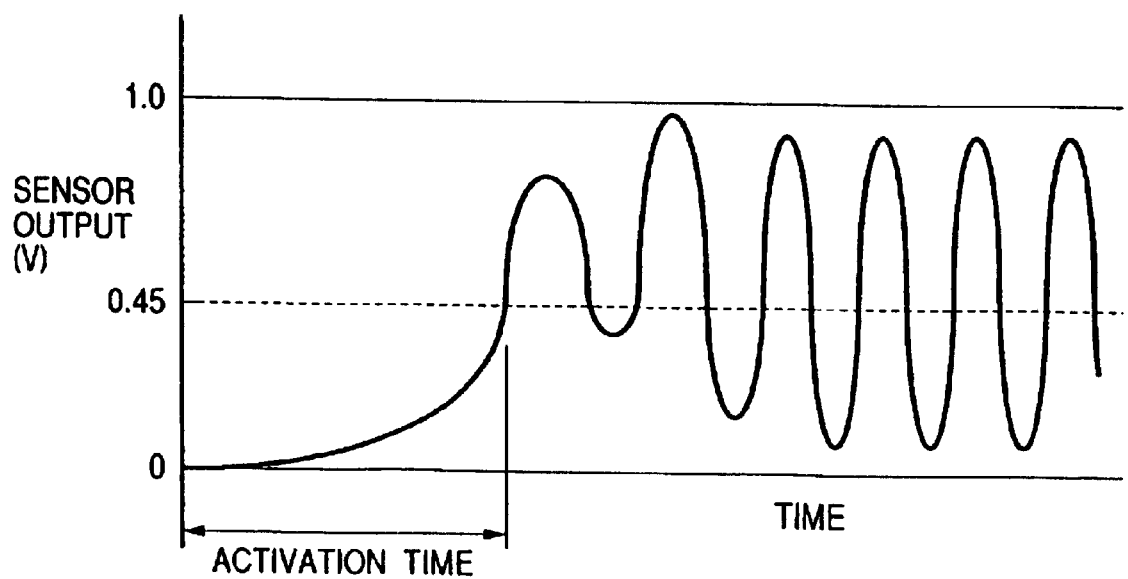
FIG. 6 is a graph showing time variation of an output signal of the gas sensor in accordance with the first embodiment of the present invention.

FIG. 6 shows a startup condition of the sensor output.

As shown in this drawing, the sensor output increases from 0V with elapsed time. An activation time is defined as a time required for the sensor output to reach 0.45V. In this case, a voltage applied to the heater 3 is 14V. This voltage was applied to the heater 3 for 10 seconds.

Figure 7:
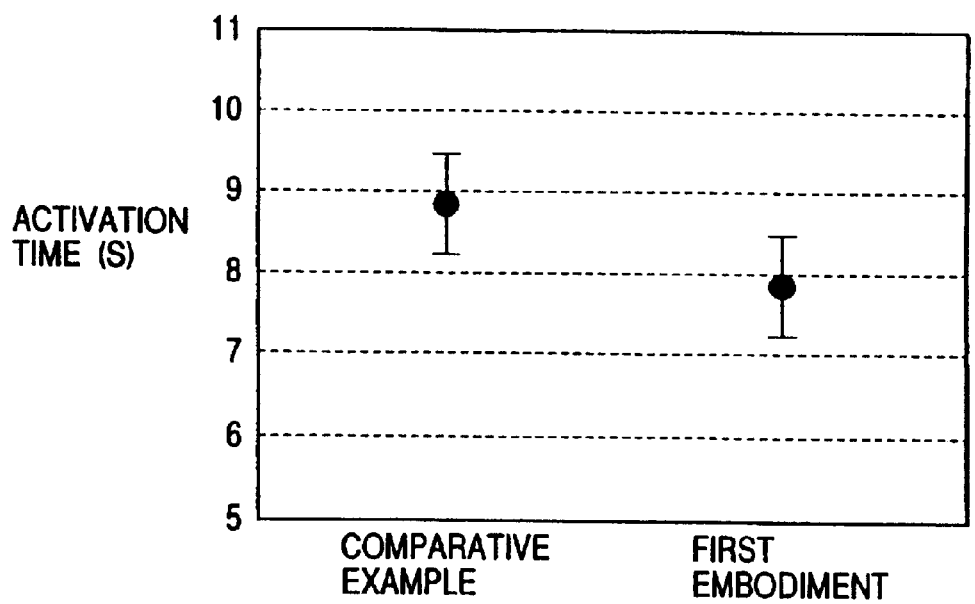
FIG. 7 is a graph showing comparison of activation time between a comparative example and the first embodiment of the present invention.

FIG. 7 shows measured result of the activation time obtained from the gas sensor of this embodiment and from the gas sensor of the comparative example.

As shown in this drawing, the activation time of the gas sensor of this embodiment is shorter than the activation time of the gas sensor of the comparative example.

Regarding the effects of heat generation in response to electric supply, the durability of the heater was measured in the following manner.

Numerous heater samples were prepared for this embodiment and for the comparative example. Each heater sample was inserted and placed in the gas sensing element, and was subjected to the 10-second voltage application of 11V to 21V.

Figure 8:
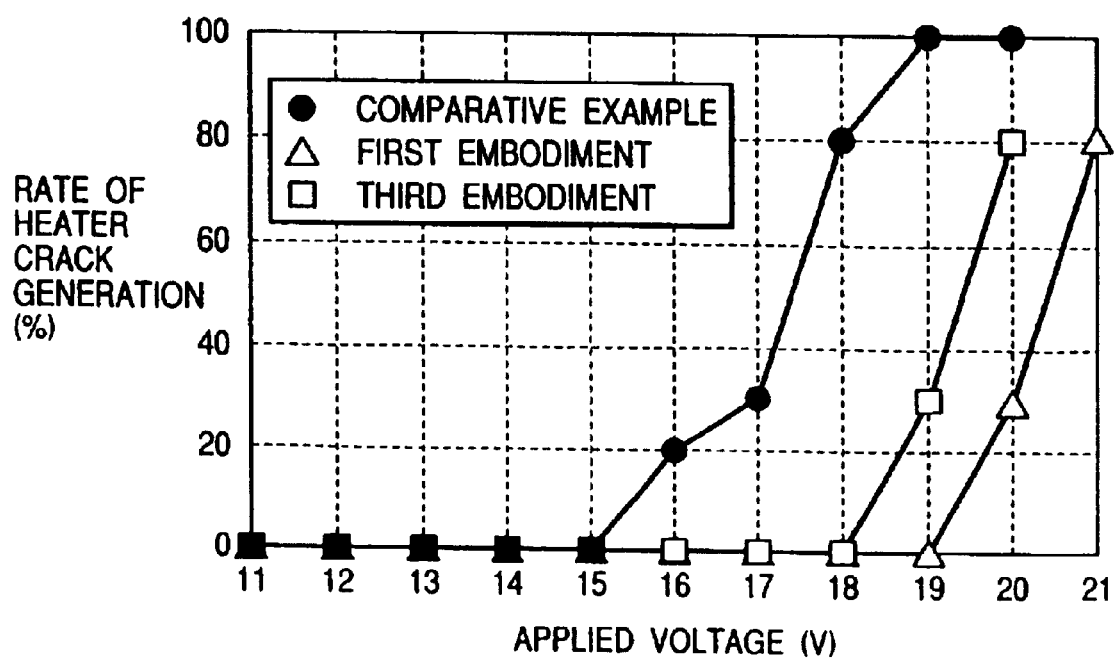
FIG. 8 is a graph showing the relationship between the rate of heater crack generation and an applied voltage in accordance with the first and third embodiments of the present invention.

FIG. 8 is a graph showing the generation rate of cracks caused in the heater samples, wherein an abscissa represents an applied voltage and an ordinate represents the generation rate of cracks.

From the obtained result shown in FIG. 8, it is understood that the heater according to this embodiment is robust against generation of cracks.

Next, functions and effects of this embodiment will be explained.

According to the gas sensor 1 of this embodiment, the heat generating peak position of the heater 3 is in the vicinity of the contact portion 30.

The generated heat of the heater 3 can be effectively used to warm up the gas sensing element 1. Thus, it becomes possible to realize the prompt activation without adverse effects of heat generation or thermal shock including deterioration of the gas sensing element and the heater.

Thus, according to this embodiment, it becomes possible to provide a gas sensor capable of realizing prompt activation without causing adverse effects of heat generation, such as thermal shock.

Although the above-described embodiment changes the width of the heat generating section to intentionally shift the heat generating peak position, the same effects will be obtained by employing the following heat generating section.

Figure 9:
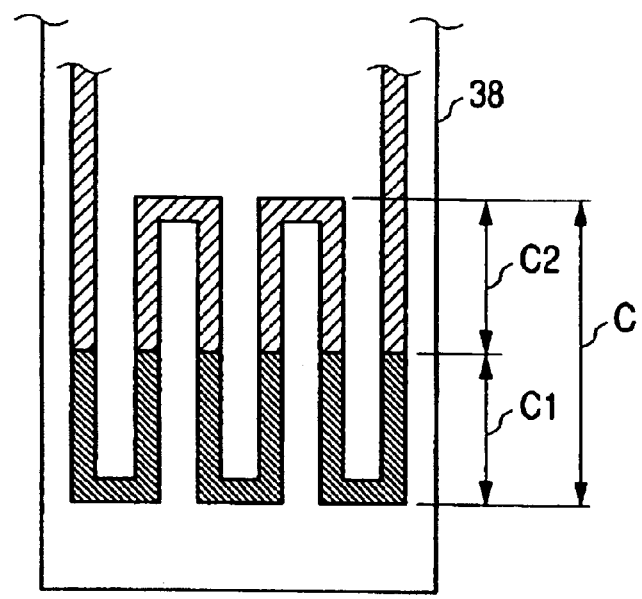
FIG. 9 is a view showing a heat generating section made of a different material in accordance with the first embodiment of the present invention.

FIG. 9 shows a region "C" indicating the heat generating section 31. The region "C" includes a distal region C1 and a proximal region C2. The distal region C1 is made of a W—Re alloy, and the proximal region C2 is made of a Mo alloy or W. A resistance value of the distal region C1 is 1.2 Ω, and a resistance value of the proximal region C2 is 1.0 Ω. Both of the distal region C1 and the proximal region C2 have the same axial length of 3 mm.

The arrangement of the gas sensor shown in FIG. 9 realizes a heat generating peak position substantially identical with that of the heat generating section 31 shown in FIG. 4A, bringing functions and effects similar to those of the above-described embodiment.

Second Embodiment

Figure 10:
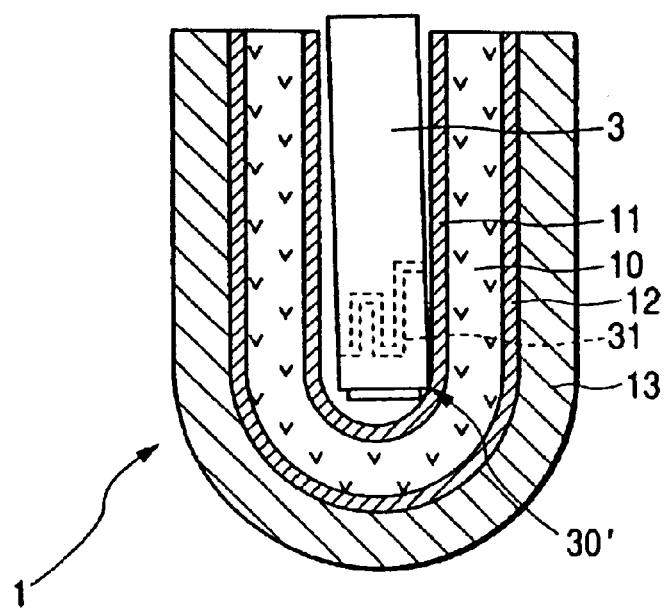
FIG. 10 is a cross-sectional view showing a gas sensing element in accordance with a second embodiment of the present invention, wherein a heater is non-coaxial (inclined) with respect to a center of a gas sensing element.

A second embodiment, as shown in FIG. 10, proposes a gas sensor having a heater disposed non-coaxially with respect to the gas sensing element.

FIG. 10 shows a positional relationship of the heater 3 with respect to the gas sensing element 1.

The heater 3 inclines with respect to the reference gas chamber 100. A contact point 30' of the heater 3 is a local spot which is brought into contact with the inside surface of the reference gas chamber 100 at a right side of the drawing.

Like the first embodiment shown in FIG. 3, the heater 3 comprises a ceramic core rod 39 and a ceramic sheet 38 wound around the ceramic axial core rod 39.

Figure 11:
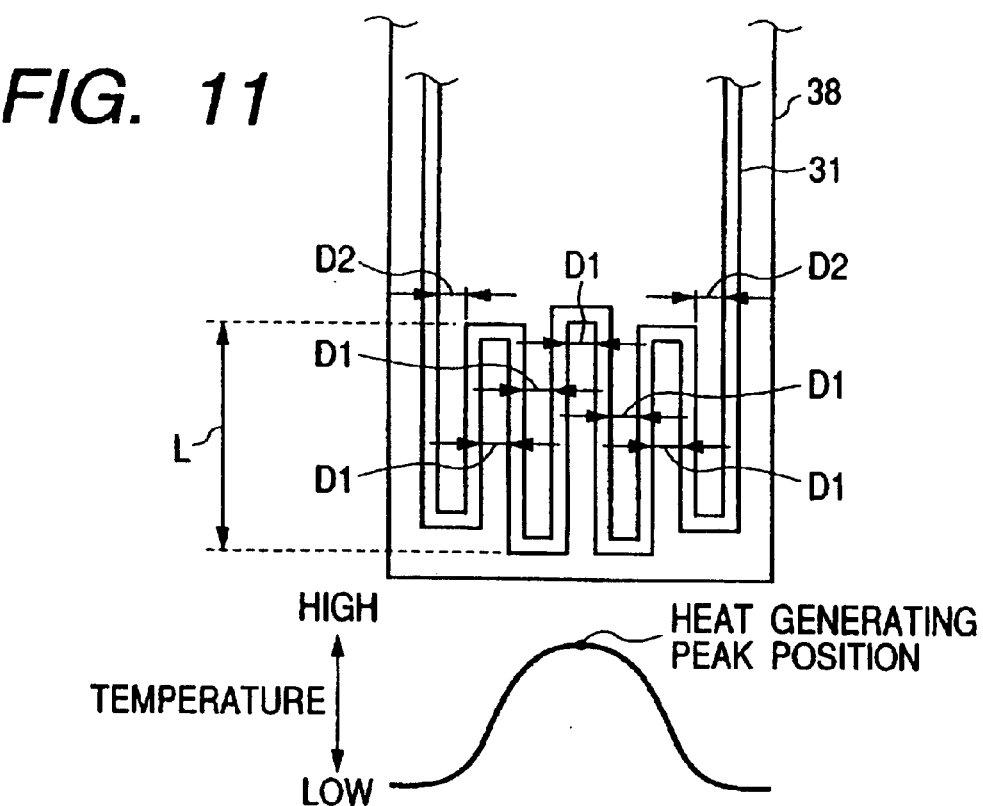
FIG. 11 is a development view showing the configuration of a heat generating section of a heater in accordance with the second embodiment of the present invention.

FIG. 11 shows the configuration of the heat generating section 31 provided on the ceramic sheet 38.

The heat generating section 31, as shown in the drawing, comprises neighboring heater lines spaced at a pitch D1 and neighboring heater lines spaced at a pitch D2, where D1<D2.

In other words, the heat generating pattern of the heat generating section 31 is locally concentrated at a portion where the pitch of neighboring heater lines is relatively short. Thus, in the circumferential direction, the heat generating peak of the heater 3 appears at this concentrated portion as shown in FIG. 11. In the drawing, L represents an axial length of the heat generating portion. According to this embodiment, L=6 mm.

Accordingly, the heat generating peak position is formed at a local spot on a cylindrical surface of the heater 3 in the circumferential direction. The heat generating peak position is in the vicinity of the contact point 30'. Thus, generated heat of the heater 3 is smoothly transferred to the gas sensing element 1 and therefore can be effectively used to warm up the gas sensing element 1.

The rest of the sensor arrangement of the second embodiment is identical with that of the first embodiment. The functions and effects identical with those of the first embodiment can be obtained.

Third Embodiment

Figure 12:
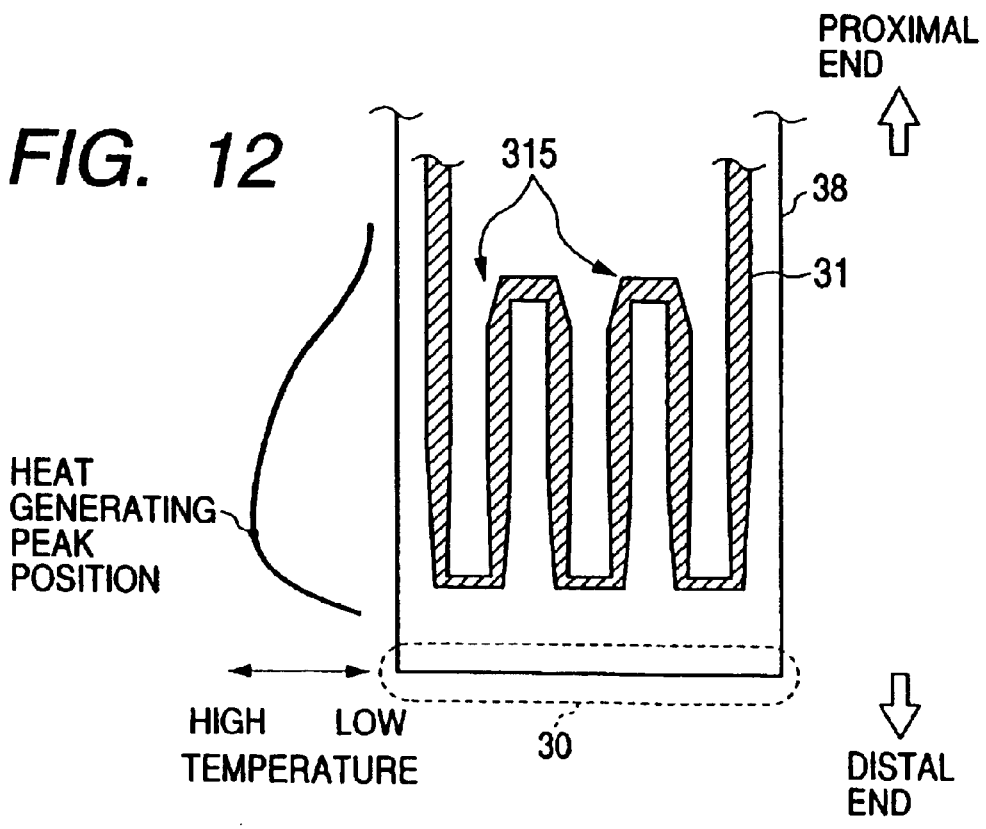
FIG. 12 is a development view showing the configuration of a heat generating section of a heater in accordance with a third embodiment of the present invention.

FIG. 12 shows a heat generating section 31 of a heater in accordance with the third embodiment of the present invention.

According to the heater of the third embodiment, the heat generating section 31 generates heat in response to electric power supplied thereto. The heat generating section 31 includes a high resistive portion 315 partly formed at the proximal side thereof. The high resistive portion 315 has a narrow width.

The rest of the sensor arrangement of the third embodiment is identical with that of the first embodiment.

Numerous heater samples were prepared for this embodiment. Each heater sample was inserted and placed in the gas sensing element, and was subjected to the 10-second voltage application of 11V to 21V.

FIG. 8 shows the generation rate of cracks caused in the heater sample of the third embodiment togther with the result of the first embodiment.

In this manner, by providing the high resistive portion 315 at the proximal end of the heat generating section 31, the heat generating peak can be moderated so as not to cause sudden increase as shown in FIG. 12. The temperature increase in the vicinity of the heat generating peak can be suppressed. An overall temperature distribution becomes uniform.

Accordingly, not only the prompt activation is realized but the heater becomes robust against the thermal shock including cracks caused by steep temperature increase at the heat generating peak position as understood from FIG. 8. The functions and effects identical with those of the first embodiment can be obtained.

Fourth Embodiment

A gas sensor of a fourth embodiment is structurally similar to the gas sensor shown in FIG. 1. The gas sensor of the fourth embodiment comprises a gas sensing element which includes a cup-shaped cylindrical solid electrolytic element having a reference gas chamber defined therein, a measured gas sensing electrode provided on an outer surface of the solid electrolytic element, and a reference gas sensing electrode provided on an inner surface of the solid electrolytic element facing the reference gas chamber. A heater is accommodated in the reference gas chamber.

The heater has a heat generating section generates heat in response to electric power supplied thereto. A contact portion is provided on an outer cylindrical surface of the heater so that the heater is brought into contact at the contact portion with an inside surface of the reference gas chamber.

According to the gas sensor in accordance with the fourth embodiment, a heat generating peak position of the heater appears within ¾ of a line segment extending between a distal end of a heat generating pattern closer to the contact portion and a center of the heat generating pattern for more than one fifth of a time required for the heat generating peak position of the heater to reach 900° C.

Figure 13:
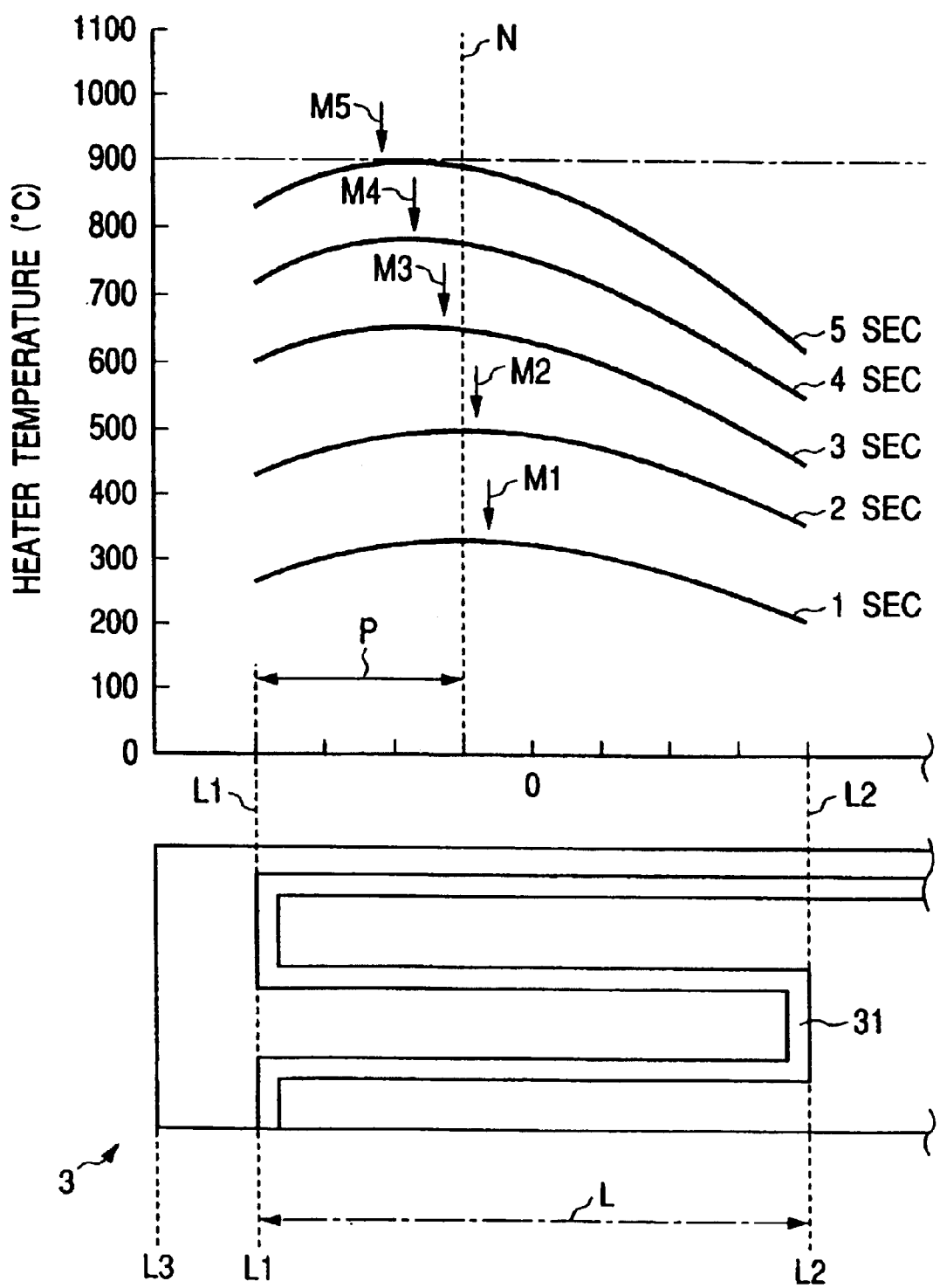
FIG. 13 is a diagram showing temperature profiles observed when electric power is suppled to a heater in accordance with a fourth embodiment of the present invention.

FIG. 13 is a diagram showing temperature profiles of the heat generating section of the gas sensing element measured at intervals of 1 second after starting supply of electric power.

In FIG. 13, "O" represents the center of the heat generating section. M1, M2, . . . M5 show heat generating peak positions of respective temperature profiles observed at the 1-second intervals. The heat generating peak position is a position where the temperature of the heater is maximized. L represents an axial length of the heat generating pattern. L1 represents a distal end of the heat generating pattern, and L2 represents a proximal end of the heat generating pattern. L3 represents the contact portion where the outer cylindrical surface of the heater is brought into contact with the inside surface of the reference gas chamber, although not clearly shown in the drawing. According to this embodiment, L is 6 mm.

As apparent from FIG. 13, the gas sensing element of the fourth embodiment requires 5 seconds to reach 900° C. at its heat generating peak position. "P" represents ¾ of a line segment L1-O extending from the distal end of the heat generating pattern closer to the contact position to the center "O" of the heat generating pattern. A dotted line N represents the ¾ position depicted with respect to the line segment L1-O. The region P is a region extending from the distal end L1 to the dotted line N.

According to the temperature profiles shown in FIG. 13, M3 to M5 are positioned within the region P.

A test for the gas sensor incorporating the above-described sensing element was conducted to evaluate activation time and durability in the same manner as in the first embodiment. According to this test, it was confirmed that the activation time is short and the gas sensing element is robust against cracks.

The rest of the gas sensor structure is substantially the same as that of the first embodiment. The functions and effects identical with those of the first embodiment can be obtained.

Fifth Embodiment

A gas sensor of the fifth embodiment is structurally similar to the gas sensor shown in FIG. 1 except for the configuration of a heat generating section.

Figure 14:
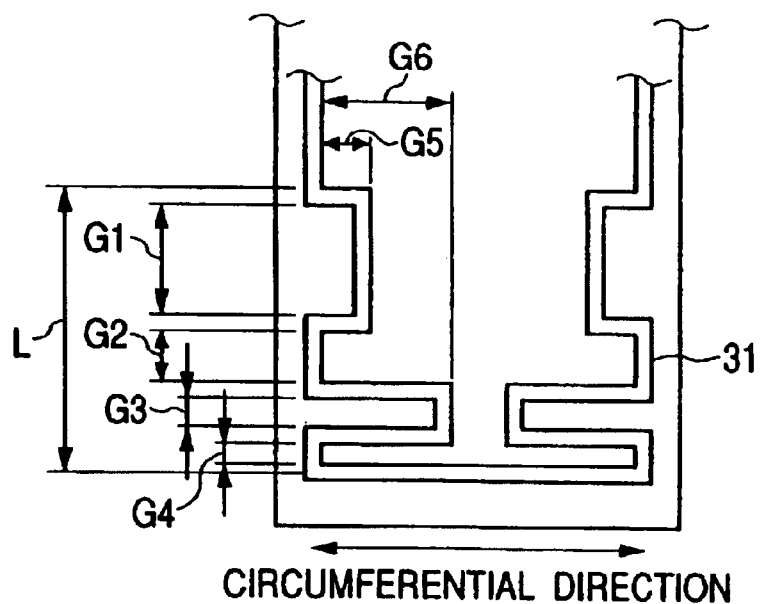
FIG. 14 is a development view showing the configuration of a heat generating section of a heater in accordance with a fifth embodiment of the present invention.

FIG. 14 shows a heat generating section 31 of the fifth embodiment which has a heater line pattern extending in a circumferential direction, not in an axial direction, of the heater. The heater line is alternately folded at relatively different pitches. G1 to G4 represent axial pitches of the heater line pattern at respective axial sections aligned from the distal end to the proximal end of the heat generating section 31. A relationship G1>G2>G3>G4 is established. G5 and G6 represent circumferential pitches of the heater line pattern at respective circumferential sections thereof. A relationship G5<G6 is established.

When the above-described relationships G1>G2>G3>G4 and G5<G6 are satisfied, the heater line pattern density of the heat generating section 31 increases at the distal end side. Accordingly, it becomes possible to increase a heat generation amount in response to supplied electric power. The gas sensing element can be promptly warmed up.

Sixth Embodiment

A gas sensor of the sixth embodiment is structurally similar to the gas sensor shown in FIG. 1 except for the configuration of a heat generating section. The gas sensor of the sixth embodiment is similar to the that of the second embodiment in that a heater is inclined with respect to the gas sensing element.

Figure 15:
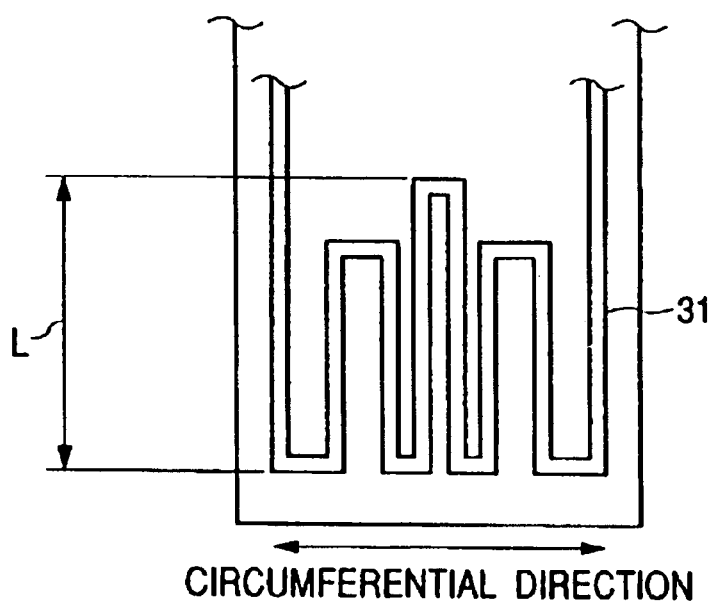
FIG. 15 is a development view showing the configuration of a heat generating section of a heater in accordance with a sixth embodiment of the present invention.

FIG. 15 shows a heat generating section 31 of the sixth embodiment which has a heater line pattern not only concentrated at a contact point (refer to 30' shown in FIG. 10)

in a circumferential direction but also concentrated at a distal end side of the heat generating section 31 in an axial direction. The axial length L of the heat generating section 31 is 6 mm.

By concentrating the heater line pattern at the distal end side in this manner, the heat generating peak is positioned on the same circumferential portion where the contact point of the heater is brought into contact and is positioned at the distal end side of the heater.

This arrangement realizes highly efficient heat transfer from the contact point of the heater to the gas sensing element. Additionally, the effect of heat radiation in the vicinity of the contact point can be enhanced. Thus, prompt activation is effectively realized.

The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising:

a gas sensing element including a cup-shaped cylindrical solid electrolytic element having a reference gas chamber defined therein, a measured gas sensing electrode provided on an outer surface of said solid electrolytic element, and a reference gas sensing electrode provided on an inner surface of said solid electrolytic element facing said reference gas chamber, and a heater accommodated in said reference gas chamber, wherein a contact portion is provided on an outer cylindrical surface of said heater so that said contact portion is brought into contact with an inside surface of said reference gas chamber, a heat generating peak position of said heater being in the vicinity of said contact portion, said heater having a heat generating section for generating heat in response to electric power supplied thereto, and said heat generating section has a high resistive portion provided at a proximal end side thereof.

2. A gas sensor comprising:

a gas sensing element including a cup-shaped cylindrical solid electrolytic element having a reference gas chamber defined therein, a measured gas sensing electrode provided on an outer surface of said solid electrolytic element, and a reference gas sensing electrode provided on an inner surface of said solid electrolytic element facing said reference gas chamber, and a heater accommodated in said reference gas chamber, wherein a contact portion is provided on an outer cylindrical surface of said heater so that said contact portion is brought into contact with an inside surface of said reference gas chamber, a heat generating peak position of said heater is in the vicinity of said contact portion, said heater has a heat generating section for generating heat in response to electric power supplied thereto, and said heat generating section has a high resistive portion at a distal end side thereof and another high resistive portion at a proximal end side thereof.

* * * * *